US 11,413,384 B2

(12) United States Patent
Loercher et al.

(10) Patent No.: US 11,413,384 B2
(45) Date of Patent: Aug. 16, 2022

(54) CAPILLARY DIALYZER

(71) Applicant: GAMBRO LUNDIA AB, Lund (SE)

(72) Inventors: Joachim Loercher, Moessingen (DE);
Juergen Eichinger, Bisingen (DE);
Reinhold Buck, Alleshausen (DE);
Arnd Wochner, Dotternhausen (DE)

(73) Assignee: GAMBRO LUNDIA AB, Lund (SE)

( * ) Notice: Subject to any disclaimer, the term of this patent is extended or adjusted under 35 U.S.C. 154(b) by 0 days.

(21) Appl. No.: 16/762,623

(22) PCT Filed: Dec. 10, 2018

(86) PCT No.: PCT/EP2018/084128
§ 371 (c)(1),
(2) Date: May 8, 2020

(87) PCT Pub. No.: WO2019/115439
PCT Pub. Date: Jun. 20, 2019

(65) Prior Publication Data
US 2020/0276373 A1    Sep. 3, 2020

(30) Foreign Application Priority Data
Dec. 11, 2017    (EP) .................... 17206463

(51) Int. Cl.
*A61M 1/16*    (2006.01)
*B01D 61/28*    (2006.01)

(52) U.S. Cl.
CPC ........ *A61M 1/1627* (2014.02); *A61M 1/1686* (2013.01); *B01D 61/28* (2013.01); *B01D 2313/20* (2013.01); *B01D 2313/21* (2013.01)

(58) Field of Classification Search
CPC .... A61M 1/1627; A61M 1/1686; A61M 1/16; B01D 61/28; B01D 2313/20; B01D 2313/21; B01D 2313/44; B01D 69/02; B01D 63/02
See application file for complete search history.

(56) References Cited

U.S. PATENT DOCUMENTS

| 5,236,586 A * | 8/1993 | Antoni .................. B01D 63/02 |
| | | 210/321.8 |
| 5,591,344 A | 1/1997 | Kenley et al. |
| 6,830,685 B2 * | 12/2004 | Pope .................... B01D 63/022 |
| | | 210/321.6 |
| 7,014,765 B2 * | 3/2006 | Dannenmaier ........ B01D 63/02 |
| | | 210/321.78 |
| 2006/0243653 A1 | 11/2006 | Bernd et al. |

FOREIGN PATENT DOCUMENTS

| DE | 19655227 | 8/2009 |
| EP | 0355325 | 2/1990 |
| EP | 3238758 | 11/2017 |
| WO | WO2013190022 | 6/2012 |

OTHER PUBLICATIONS

PCT Search Report and Written Opinion prepared for PCT/EP2018/084128, completed Jan. 28, 2019.

* cited by examiner

*Primary Examiner* — Krishnan S Menon
(74) *Attorney, Agent, or Firm* — Barnes & Thornburg LLP

(57) ABSTRACT

The present disclosure relates to capillary dialyzers for blood purification, in particular, capillary dialyzers suitable for home hemodialysis systems.

10 Claims, 2 Drawing Sheets

CAPILLARY DIALYZER

CROSS-REFERENCE TO RELATED APPLICATIONS

This application is the U.S. national phase of PCT/EP2018/084128, filed on Dec. 10, 2018, which claims the benefit of European Patent Application Serial Number 17206463.6, filed on Dec. 11, 2017, the entire disclosures of both of which are incorporated herein by reference.

TECHNICAL FIELD

The present disclosure relates to capillary dialyzers for blood purification, in particular, capillary dialyzers suitable for home hemodialysis systems.

BACKGROUND OF THE INVENTION

Capillary dialyzers are widely used for blood purification in patients suffering from renal insufficiency, i.e., for treatment of the patients by hemodialysis, hemodiafiltration or hemofiltration. A multitude of different models of capillary dialyzers is commercially available.

The devices generally consist of a casing comprising a tubular section with end caps capping the mouths of the tubular section. A bundle of hollow fiber membranes is arranged in the casing in a way that a seal is provided between the first flow space formed by the fiber cavities and a second flow space surrounding the membranes on the outside. Examples of such devices are disclosed in EP 0 844 015 A2, EP0 305 687 A1, and WO 01/60477 A2.

There is a continuing desire to further improve such capillary dialyzers, e.g., in terms of performance, efficiency, reliability, safety, handling, and other properties. Especially capillary dialyzers used in home hemodialysis systems must be able to withstand treatments with extended duration (e.g., nocturnal dialysis treatment), multiple treatment cycles, and multiple disinfection cycles.

SUMMARY OF THE INVENTION

It is an object of the present invention to provide capillary dialyzers with improved properties which can be used in home hemodialysis systems.

The capillary dialyzers of the present invention are particularly suitable for use in home hemodialysis, as they are designed to be used repeatedly in treatments of the same patient. The capillary dialyzers withstand multiple treatment and disinfection cycles.

SHORT DESCRIPTION OF THE DRAWINGS

DETAILED DESCRIPTION

Figure 1:
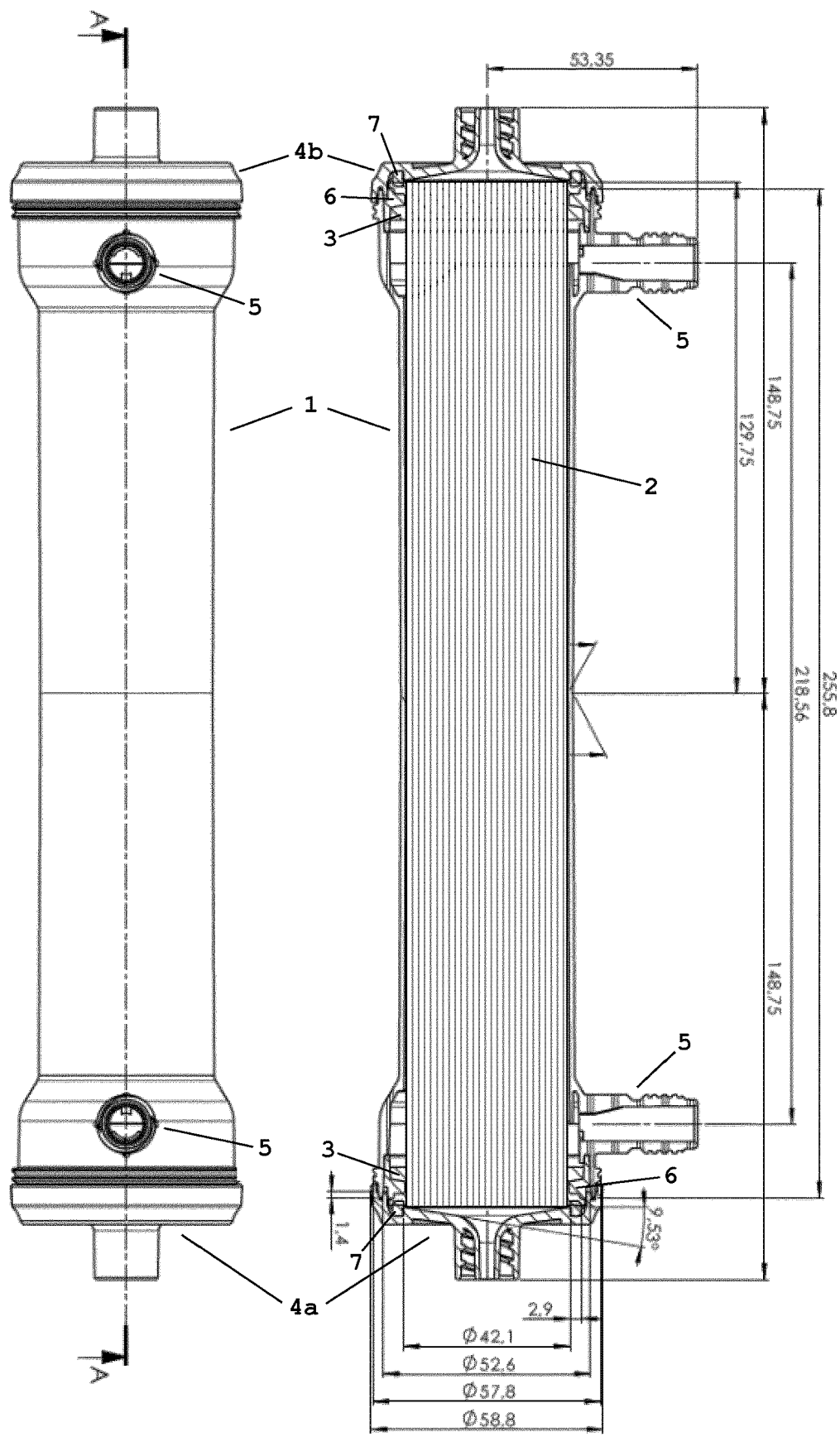
FIG. 1 shows a side view and a partially cross-sectional view of an embodiment of the capillary dialyzer of the present application.

A subject of the present disclosure is a capillary dialyzer comprising:
a) a housing defining a longitudinally extending internal chamber including a first end and a second end;
b) a bundle of semi-permeable hollow fiber membranes disposed within the internal chamber and extending longitudinally from the first end of the housing to the second end of the housing, the hollow fiber membranes having an outer surface, and a first end and a second end corresponding to the first end and the second end of the internal chamber;
c) end wall means supporting the first and second ends of the hollow fiber membranes within the internal chamber so as to sealingly separate the first and second ends of the hollow fiber membranes from the outer surface of the hollow fiber membranes between the first and second ends thereof;
d) a first end cap covering the first end of the housing and a second end cap covering the second end of the housing, the first and second end caps being applied to the first and second ends of the housing in a fluid-tight manner;
e) an inlet for the introduction of a fluid into the internal chamber and an outlet for the evacuation of a fluid from the internal chamber at a location between the first and second end of the housing;
f) support rings disposed between the end wall means and the housing at the first and second ends of the internal chamber; and
g) sealing rings interposed between the end wall and the first end cap and between the end wall and the second end cap, respectively.

The capillary dialyzer of the present disclosure is characterized in that the semi-permeable hollow fiber membranes each have an inner diameter in the range of from 185 µm to less than 195 µm, for instance, 188 µm to 192 µm, and a wall thickness in the range of from 45 µm to 55 µm, for instance, 48 µm to 52 µm; and the packing density of the hollow fiber membranes in a middle section of the housing is in the range of from 52% to 54%.

The packing density of the hollow fiber membranes in the capillary dialyzers of the present disclosure is in the range of from 52% to 54%, i.e., the sum of the cross-sectional area of all hollow fiber membranes present in the dialyzer amounts to 52% to 54% of the cross-sectional area of the middle section of the dialyzer housing. If n hollow fiber membranes are present in the dialyzer, $D_F$ is the outer diameter of a single hollow fiber membrane, and $D_H$ is the inner diameter of the middle section of the dialyzer housing, the packing density can be calculated per $n*(D_F/D_H)^2$.

In one embodiment, the capillary dialyzer comprises from 10,200 to 11,000 hollow fiber membranes; the effective surface area of the hollow fiber membranes totaling from 1.45 to 1.55 m$^2$.

It has been found that the particular hollow fiber membranes employed in the capillary dialyzer of the present disclosure and the packing density impart improved durability to the dialyzer. It is hypothesized that the particular ratio of wall strength to inner diameter of the hollow fiber membranes in combination with the particular packing density of the hollow fiber membranes in the housing enable the fibers to better withstand the multitude of pressure swings occurring during treatment, thus reducing the incidence of fiber ruptures. In a typical setting, the capillary dialyzer of the present disclosure is used in up to 30 treatments, each lasting 10 hours. It is subjected to up to 30 heat disinfection cycles with hot water (90-95° C., 2-3 hours). During its use, it is subjected to more than 300,000 pressure swings with a differential pressure of more than 1 bar.

The semipermeable hollow fiber membranes are preferably based on at least one hydrophobic polymer and on at least one hydrophilic polymer. Said at least one hydrophobic polymer is preferably chosen from the group consisting of polyamide (PA), polyaramide (PAA), polyarylethersulfone (PAES), polyethersulfone (PES), polysulfone (PSU), polyarylsulfone (PASU), polycarbonate (PC), polyether, polyurethane (PUR), polyetherimide and copolymers of said polymers, preferably polyethersulfone or a mix of polyarylethersulfone and polyamide. Polyethersulfone and polysulfone are preferred for use hydrophobic polymers. Preferably, polyethersulfone is used for preparing the hollow fiber membranes of the present disclosure.

An example of a suitable polyethersulfone is a polymer having the general formula —[O—Ph—$SO_2$—Ph—]$_n$—, a weight average molecular weight of about 60,000 to 65,000 Da, preferably 63,000 to 65,000 Da, and a $M_w/M_n$ of about 1, 5 to 1, 8.

Said at least one hydrophilic polymer is preferably chosen from the group consisting of polyvinylpyrrolidone (PVP), polyethyleneglycol (PEG), polyglycolmonoester, water soluble cellulosic derivates, polysorbate and polyethylene-polypropyleneoxide copolymers. Preferably, polyvinylpyrrolidone is used for preparing the hollow fiber membranes of the present disclosure, wherein the polyvinylpyrrolidone consists of a low molecular weight component having a molecular weight of below 100 kDa and a high molecular weight component having a molecular weight of 100 kDa or more.

A preferred embodiment of the semipermeable hollow fiber membrane consists of 80-99% by weight of said hydrophobic polymer, preferably polyethersulfone, and 1-20% by weight of said at least one hydrophilic polymer, preferably polyvinylpyrrolidone (PVP). The PVP consists of a high (≥100 kDa) and low (<100 kDa) molecular component, wherein the PVP consists of 10-45 weight-% based on the total weight of PVP in the membrane, of a high molecular weight component, and of 55-90 weight-% based on the total weight of PVP in the membrane, of a low molecular weight component.

The spinning solution for preparing the semipermeable hollow fiber membranes preferably comprises between 12 and 15 weight-% of polyethersulfone or polysulfone as hydrophobic polymer and 5 to 10 weight-% of PVP, wherein said PVP consists of a low and a high molecular PVP component. The total PVP contained in the spinning solution consists of between 22 and 34 weight-% and preferably of between 25 and 30 weight-% of a high molecular weight component and of between 66 and 78 weight-%, preferably of between 70 and 75 weight-% of a low molecular weight component. Examples for high and low molecular weight PVP are, for example, PVP K85/K90 and PVP K30, respectively.

The polymer solution used for preparing the semipermeable hollow fiber membranes of the present disclosure preferably further comprises 66-86% by weight solvent and 1-5% by weight suitably additives. Suitable additives are, for example, chosen form the group of water, glycerol and/or other alcohols. Water is especially preferred in the context of the present invention and is present in the spinning solution in an amount of between 1-8% by weight, preferably in an amount of between 2-5% by weight. The solvent used in the process of the present invention preferably is chosen from the group comprising N-methylpyrrolidone (NMP), dimethylacetamide (DMAC), dimethylsulfoxide (DMSO), dimethylformamide (DMF), butyrolactone and mixtures of said solvents. NMP is especially preferred in the context of the present invention. The spinning solution should be homogenously degassed and filtered.

In a particular embodiment, the spinning solution comprises 14 wt. % polyethersulfone, 2 wt. % high molecular weight PVP, 5 wt. % low molecular weight PVP, 3 wt. % water, and 76 wt. % NMP.

The center fluid or bore liquid which is used for preparing semipermeable hollow fiber membranes of the present disclosure comprises at least one of the above-mentioned solvents and a precipitation medium chosen from the group of water, glycerol and other alcohols. Most preferably the center fluid consists of 45-70% by weight of the precipitation medium, and 30-55% by weight of the solvent. Preferably, the center fluid consists of 51-57% by weight of water and 43-49% by weight of NMP. In a particular embodiment, the center fluid consists of 45.5 wt. % NMP and 55.5 wt. % water. Again, the center fluid should be degassed and filtered.

In one embodiment, the viscosity of the polymer solution is in the range of from 2,500 to 7,000 mPa·s, preferably from 3,500 to 5,500 mPa·s.

In a preferred embodiment of the process, the temperature of the spinneret is 30-70° C., preferably 50-58° C., and the temperature of the spinning shaft is 25-65° C., preferably 45-55° C. In a particular embodiment, the temperature of the spinneret is 55±1° C., and the temperature of the spinning shaft is 52±1° C.

In one embodiment of the process, the distance between the opening of the nozzle and the precipitation bath is between 25 and 1500 mm, preferably between 550 and 1100 mm. The precipitation bath has a temperature of 10-40° C., preferably of 15-25° C.

In one embodiment of the process, the spinning velocity is in the range of from 25 to 80 m/min, preferably from 30 to 60 m/min. In a particular embodiment, the spinning velocity is 45 m/min.

The semipermeable hollow fiber membranes of the present disclosure will then preferably be washed in water to remove waste components, and then be dried at temperatures between 150-250° C., preferably between 180-220° C. Such drying will provide for an adequate evaporation of water and a defined shrinkage of pores. The final treatment consists of rinsing the membrane in water at a temperature of 50-95° C., preferably 80-90° C. and subsequent drying at temperatures of 30-65° C., preferably 55-65° C.

The membrane is preferably steam sterilized at temperatures above 121° C. for at least 21 minutes.

In one embodiment, the hollow fiber membranes are asymmetric and have a four-layer structure.

The inner layer of the four-layer structure, i.e. the blood contacting layer and the inner surface of the hollow fiber membrane, is a separation layer in the form of a dense thin layer having, in one embodiment, a thickness of less than 1 µm and a pore size in the nano-scale range. To achieve high selectivity, the pore channels with the responsible pore diameters are short, i.e. below 0.1 µm. The pore channel diameter has a low variation in size.

The next layer in the hollow fiber membrane is the second layer having the form of a sponge structure and, in one embodiment of the present invention, a thickness of about 1 to 15 µm, and serves as a support for the first layer.

The third layer has the form of a finger structure. It provides for mechanical stability on the one hand; on the other hand, it has, due to the high void volume, a very low resistance of transport of molecules through the membrane when the voids are filled with water. The third layer has, in one embodiment of the present invention, a thickness of 20 to 50 µm.

The fourth layer is the outer layer, which is characterized by a homogeneous and open pore structure with a defined surface roughness. In one embodiment, the number average size of the pore openings is in the range of 0.5 to 3 μm, further the number of pores on the outer surface is in the range of 20,000 to 100,000 pores per mm². In one embodiment, this fourth layer has a thickness of about 1 to 10 μm.

In one embodiment, the capillary dialyzers of the present invention show sieving coefficients of 1.0 for vitamin B12, 1.0 for inulin, 0.7 for β2-microglobulin, and less than 0.01 for albumin.

The particular design of the housing and the end caps of the capillary dialyzer of the present disclosure also enhance the durability of the dialyzer.

In one embodiment, the ratio of the inner diameter of the middle section of the housing to the overall length of the housing is smaller than 0.17 in the capillary dialyzer.

In one embodiment, the inner diameter of the middle section of the housing of the capillary dialyzer is 41.0±0.1 mm and the length of the housing is 255.8±0.1 mm.

It is hypothesized that the particular ratio of the inner diameter of the housing to its length reduces the strain on the fiber bundle during use and helps the fibers to better withstand the pressure swings occurring during treatment, thus reducing the incidence of fiber ruptures.

In one embodiment, the inner diameter of the middle section of the housing of the capillary dialyzer is 41.0±0.1 mm and the inner diameter of the mouth of the housing of the capillary dialyzer is 52.6±0.1 mm.

In one embodiment, the ratio of the wall thickness of the housing to the inner diameter of the middle section of the housing to the overall length is larger than 0.03 in the capillary dialyzer.

It is hypothesized that the particular ratio of the wall thickness to the inner diameter of the housing increases the rigidity of the housing, thus limiting the amplitude of vibrations of the housing wall caused by pressure swings during use. As a result, the capillary dialyzer is less prone to leakage caused by crack formation in the shell of the dialyzer. Likewise, the relative size of the inner diameters of the middle section of the housing and the mouth of the housing, respectively, result in a favorable pressure distribution within the dialyzer.

In one embodiment, the capillary dialyzer comprises annular protrusions on the outer surface of the housing adjacent to the end caps. The protrusions have a length, in axial direction, of in the range of 3 to 5 mm, e.g., 3 to 4 mm, and the wall strength of the housing in the area of the protrusions is in the range of from 150 to 200 percent of the wall strength adjacent to the protrusions. The term "adjacent" in the context of the present disclosure means less than 1 mm away.

It is hypothesized that the protrusions additionally increase rigidity of the housing by locally increasing the wall diameter of the housing, thus both limiting the amplitude of vibrations of the housing wall caused by pressure swings during use as well as preventing build-up of resonance vibrations leading to catastrophic failure of the housing wall.

In one embodiment of the capillary dialyzer, the end caps have an inner surface which is rotationally symmetrical with regard to a longitudinal axis of the end cap and an inner surface having the form of a funnel and comprising, in the direction of increasing diameter, a first section taking the form of at least one of a cylinder and a truncated cone, a middle section taking the form of a torus segment and having a radius R of 7.0±0.1 mm, and a third section taking the form of a truncated cone, wherein the diameter D of the base of the third section is 42.1±0.1 mm and the angle α between the base of the third section and the lateral surface of the third section is 9.53±0.05°, and the outer diameter of the end cap is 58.8±0.1 mm.

Another subject of the present disclosure is a home hemodialysis system comprising the capillary dialyzer of the present disclosure. The capillary dialyzer of the present disclosure is particularly suitable for use in home hemodialysis systems. A typical home hemodialysis system comprises a hemodialysis machine for the treatment of patients suffering from end-stage renal disease (ESRD) which can be used in the patient's home. The hemodialysis machine comprises equipment for preparation of the dialysis fluid needed for the dialysis treatment, equipment for circulating blood and dialysis fluid through the dialyzer, and equipment for performing the disinfection of the dialyzer and the tubing of the extracorporeal blood circuit. In a typical setting, the dialyzer and the tubing set of the blood circuit attached to the hemodialysis machine remain attached after a hemodialysis treatment and are reused after disinfection. They can be used for multiple subsequent treatments, e.g., up to 30 treatments. In comparison with single-use dialyzers, which are typically used in a clinical setting, the extended use of the dialyzer and the multiple disinfection cycles in a home hemodialysis system cause increased strain on the dialyzer. Leakage of the housing can result, especially at the joint of the housing to the end caps, or at the juncture of the fluid ports and the housing. The capillary dialyzer of the present disclosure is less prone to internal or external leakage than conventional dialyzers.

The use of the capillary dialyzer of the present disclosure in a home hemodialysis system also is a subject of the present disclosure. In one embodiment, the use comprises disinfecting the capillary dialyzer by flushing the dialyzer with water having a temperature in the range of from 90 to 95° C. for a time in the range of from 2 to 3 hours. As described above, the capillary dialyzer is subjected to such a heat disinfection cycle between successive hemodialysis treatments. In one embodiment, the use comprises multiple disinfections of an individual capillary dialyzer, e.g. the dialyzer is subjected to disinfection more than 10 than times, more than 20 times, or up to 30 times.

FIG. 1 shows an embodiment of the capillary dialyzer of the present disclosure comprising:
 a) a housing 1 defining a longitudinally extending internal chamber including a first end and a second end;
 b) a bundle of semi-permeable hollow fiber membranes 2 disposed within the internal chamber and extending longitudinally from the first end of the housing to the second end of the housing, the hollow fiber membranes having an outer surface, and a first end and a second end corresponding to the first end and the second end of the internal chamber;
 c) end wall means 3 supporting the first and second ends of the hollow fiber membranes within the internal chamber so as to sealingly separate the first and second ends of the hollow fiber membranes from the outer surface of the hollow fiber membranes between the first and second ends thereof;
 d) a first end cap 4a covering the first end of the housing and a second end cap 4b covering the second end of the housing, the first and second end caps being applied to the first and second ends of the housing in a fluid-tight manner;
 e) an inlet 5 for the introduction of a fluid into the internal chamber and an outlet 5 for the evacuation of a fluid from the internal chamber at a location between the first and second end of the housing;

f) support rings 6 disposed between the end wall means and the housing at the first and second ends of the internal chamber; and g) sealing rings 7 interposed between the end wall and the first end cap 4a and between the end wall and the second end cap 4b, respectively.

The diameter of the housing 1 of the capillary dialyzers of the present invention is not uniform. The housing 1 has a middle section where the inner diameter is smaller than at the ends of the housing 1. In the embodiment shown in FIG. 1, the inner diameter of the middle section of the housing 1 is 41.0±0.1 mm; and the inner diameter of the mouth of the housing 1 is 52.6±0.1 mm. The outer diameter of the middle section of the housing 1 is 43.6±0.1 mm.

The overall length of the housing 1 of the capillary dialyzer of FIG. 1 is 255.8±0.3 mm; the distance between the centers of the inlet 5 and outlet 5 is 218.56±0.3 mm.

The housing 1 and the end caps 4a, 4b of the capillary dialyzers of the present disclosure are usually made of a transparent polymer, e.g. polyethylene, polypropylene, polyesters like PET or PBT, polymethylmethacrylate, polystyrene (HIPS) or polycarbonate. The potting material for the hollow fiber membranes usually is polyurethane.

In one embodiment of the device of the invention, the housing 1 and end caps 4a, 4b are comprised of polycarbonate, the potting material forming the end wall means 3 is comprised of polyurethane, the support rings 6 are comprised of polypropylene and the sealing rings 7 are comprised of silicone rubber.

Figure 2:
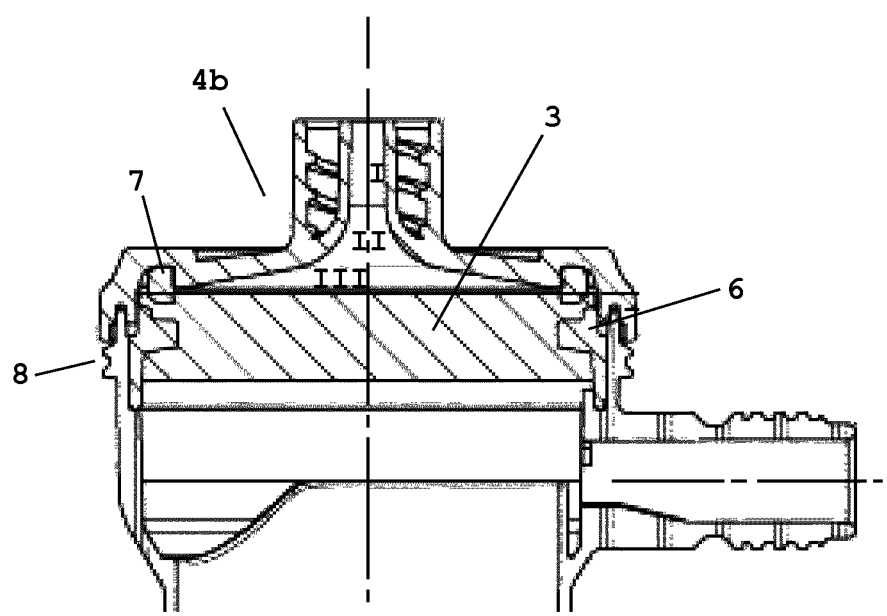
FIG. 2 shows an enlarged view of the header section of the dialyzer shown in FIG. 1.

FIG. 2 shows an enlarged view of the header section of the dialyzer shown in FIG. 1 including the end cap 4b. As shown in FIG. 2, the end cap 4b comprises an inlet or outlet, respectively, for a liquid, arranged axially in the center of the end cap 4b. A two-start thread which fits a standard bloodline connector is provided round the inlet or outlet. Starting from the mouth of the end cap 4b, the inner diameter of the inlet or outlet is constant or increases linearly in a first section I of the end cap, then widens gradually, with a constant curvature R of 7±0.1 mm, in a second section II until the inner surface includes a predetermined angle α of 9.53±0.05° with the horizontal. The diameter then increases linearly in a third section III, until a predetermined diameter D is reached. At diameter D of 42.1±0.1 mm, the fluid compartment formed by the inside of the end caps 4b and the lumen of the hollow fiber membranes 2 is sealed off by a sealing ring 7 placed in a circular groove provided in the end cap 4b. The inner surface of the end cap 4b is rotationally symmetrical about the longitudinal axis of the inlet/outlet, which is also the longitudinal axis of the end cap 4b. The inner surface has the form of a funnel comprising, in the direction of increasing diameter, a first section I taking the form of a cylinder or a truncated cone, a middle section II taking the form of a torus segment, and a third section III taking the form of a truncated cone. The outer diameter of the end cap 4b is 58.8±0.1 mm.

As shown in FIG. 2, an annular protrusion 8 is provided on the outer surface of the housing 1, adjacent to the end cap 4b, directly below the lip of the end cap 4b. The protrusion 8 locally enlarges the wall thickness of the housing 1 in this area. The wall thickness of the housing 1 within the protrusion 8 is 1.5 to 2 times the wall thickness in the area adjacent to the protrusion 8.

The dialyzer can be operated at blood flow rates in the range of from 200 to 600 ml/min and dialysate flow rates of from 300 to 800 ml/min.

When the dialyzer is operated in hemodialysis mode using a blood flow rate of 300 ml/min, a dialysate flow rate of $Q_D$=500 ml/min, and an ultrafiltration rate UF of 0 ml/min, clearance value for urea is 270 ml/min, clearance value for vitamin B12 is 173 ml/min, and protein loss is 0.39 g/L.

LIST OF REFERENCE SIGNS 1 housing
2 hollow fiber membrane
3 end wall means (potting zone)
4a first end cap
4b second end cap
5 fluid port (inlet or outlet)
6 support ring
7 sealing ring
8 protrusion

The invention claimed is:

1. A method of treating a patient using a home hemodialysis system comprising a capillary dialyzer, said method comprising the step of administering a hemodialysis session to the patient using the home hemodialysis system, wherein the capillary dialyzer of the home hemodialysis system comprises:

a) a housing defining a longitudinally extending internal chamber including a first end and a second end;

b) a bundle of semi-permeable hollow fiber membranes disposed within the internal chamber and extending longitudinally from the first end of the housing to the second end of the housing, the hollow fiber membranes having an outer surface, and a first end and a second end corresponding to the first end and the second end of the internal chamber;

c) end wall means supporting the first and second ends of the hollow fiber membranes within the internal chamber so as to sealingly separate the first and second ends of the hollow fiber membranes from the outer surface of the hollow fiber membranes between the first and second ends thereof;

d) a first end cap covering the first end of the housing and a second end cap covering the second end of the housing, the first and second end caps being applied to the first and second ends of the housing in a fluid-tight manner;

e) an inlet for the introduction of a fluid into the internal chamber and an outlet for the evacuation of a fluid from the internal chamber at a location between the first and second end of the housing;

f) support rings disposed between the end wall means and the housing at the first and second ends of the internal chamber; and g) sealing rings interposed between the end wall and the first end cap and between the end wall and the second end cap, respectively;

characterized in that the semi-permeable hollow fiber membranes each have an inner diameter in the range of from 185 μm to less than 195 μm, and a wall thickness in the range of from 45 μm to 55 μm; and the packing density of the hollow fiber membranes in a middle section of the housing is in the range of from 52% to 55%.

2. The method of claim 1, wherein the capillary dialyzer comprises from 10,200 to 11,000 hollow fiber membranes, and the effective surface area of the hollow fiber membranes totals from 1.45 to 1.55 m².

3. The method of claim 1, wherein the capillary dialyzer comprises a ratio of the inner diameter of the middle section of the housing to the overall length of the housing smaller than 0.17.

4. The method of claim 1, wherein the capillary dialyzer comprises an inner diameter of the middle section of the housing of 41.0+/−0.1 mm and a length of the housing of 255.8+/−0.1 mm.

5. The method of claim 1, wherein the capillary dialyzer comprises an inner diameter of the middle section of the housing of 41.0+/−0.1 mm and an inner diameter of the mouth of the housing of 52.6+/−0.1 mm.

6. The method of claim 1, wherein the capillary dialyzer comprises annular protrusions on the outer surface of the housing adjacent to the end caps, the protrusions having a length of 3 to 4 mm in axial direction, and the wall strength of the housing in the area of the protrusions being in the range of 150 to 200 percent of the wall strength adjacent to the protrusions.

7. The method of claim 1, wherein the end caps have an inner surface which is rotationally symmetrical with regard to a longitudinal axis of the end cap and an inner surface having the form of a funnel and comprising, in the direction of increasing diameter, a first section (I) taking the form of at least one of a cylinder and a truncated cone, a middle section (II) taking the form of a torus segment and having a radius R of 7.0+/−0.1 mm, and a third section (III) taking the form of a truncated cone, wherein the diameter D of the base of the third section (III) is 42.110.1 mm and the angle between the base of the third section and the lateral surface of the third section (III) is 9.53+/−0.05°, and the outer diameter D2 of the end cap is 58.8+/−0.1 mm.

8. The method of claim 1, wherein the dialyzer and the tubing set of the blood circuit attached to the hemodialysis machine remain attached after the hemodialysis treatment and are capable of being reused after disinfection.

9. The method of claim 8 further comprising the step of disinfecting the capillary dialyzer by flushing the dialyzer after use, wherein the flushing is performed with water having a temperature in the range of from 90 to 95° C. for a time in the range of from 2 to 3 hours.

10. The method of claim 9, wherein the capillary dialyzer is used for up to 30 hemodialysis treatments and subjected to up to 30 disinfection cycles.

\* \* \* \* \*